US012758275B2

(12) United States Patent
Biedermann et al.

(10) Patent No.: US 12,758,275 B2
(45) **Date of Patent: *Oct. 13, 2026**

(54) ADAPTER DEVICE AND SYSTEM INCLUDING AN ADAPTER DEVICE AND A BONE ANCHOR

(71) Applicant: BIEDERMANN TECHNOLOGIES GMBH & CO. KG, Donaueschingen (DE)

(72) Inventors: Timo Biedermann, Trossingen (DE); Dimosthenis Dandanopoulos, VS-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 297 days.

This patent is subject to a terminal disclaimer.

(21) Appl. No.: 18/650,821

(22) Filed: Apr. 30, 2024

(65) Prior Publication Data

US 2024/0341821 A1 Oct. 17, 2024

Related U.S. Application Data

(63) Continuation of application No. 17/553,532, filed on Dec. 16, 2021, now Pat. No. 11,992,247.

(Continued)

(30) Foreign Application Priority Data

Dec. 17, 2020 (EP) .................................... 20215224

(51) Int. Cl.

| | |
|---|---|
| ***A61B 17/70*** | (2006.01) |
| *A61B 17/00* | (2006.01) |
| *A61B 17/56* | (2006.01) |

(52) U.S. Cl.

CPC .. *A61B 17/708* (2013.01); *A61B 2017/00486* (2013.01); *A61B 2017/564* (2013.01); *A61B 17/7035* (2013.01)

(58) Field of Classification Search

CPC ............ A61B 17/7074; A61B 17/7076; A61B 17/8886; A61B 17/8891; A61B 17/888;

(Continued)

(56) References Cited

U.S. PATENT DOCUMENTS 4,763,548 A 8/1988 Leibinger et al.
5,605,080 A * 2/1997 Pfefferle ............... B25B 23/101 81/452

(Continued)

FOREIGN PATENT DOCUMENTS

DE 20 2005 012 781 U1 11/2005
EP 2 170 192 A2 4/2010

(Continued)

OTHER PUBLICATIONS

Extended European Search Report for Application No. 20215224.5, mailed Jun. 23, 2021, 8 pages.

(Continued)

*Primary Examiner* — Eduardo C Robert
*Assistant Examiner* — Michelle C Green
(74) *Attorney, Agent, or Firm* — Womble Bond Dickinson (US) LLP

(57) ABSTRACT

An adapter device for connecting an instrument to a bone anchor includes an elongate main portion having a longitudinal axis, a first end with a surface that is directly engageable with a head of the bone anchor, an opposite second end, and a channel that extends longitudinally through the main portion, and a holding member having an inner surface forming a seat for the head. The holding member is movable over a majority of the main portion, and is configured to be (Continued)

held at a position where a first portion of the seat is directed towards the second end of the main portion to hold the head in the seat against the first end of the main portion, while the holding member engages another part of the adapter device to keep the first portion of the seat spaced apart axially from the first end of the main portion.

20 Claims, 9 Drawing Sheets

Related U.S. Application Data

(60) Provisional application No. 63/126,758, filed on Dec. 17, 2020.

(58) Field of Classification Search
CPC ............ A61B 17/8875; A61B 17/8872; A61B 17/8841; A61B 17/8819
See application file for complete search history.

(56) References Cited

U.S. PATENT DOCUMENTS 5,649,931 A * 7/1997 Bryant ............... A61B 17/8891 606/104
5,667,513 A 9/1997 Torrie et al.
6,189,422 B1 * 2/2001 Stihl ....................... B25B 15/02 81/452
7,354,442 B2 4/2008 Sasso et al.
7,717,947 B1 5/2010 Wilberg et al.
8,821,506 B2 9/2014 Mitchell
10,285,740 B2 * 5/2019 May ................... A61B 17/1637
11,116,559 B2 * 9/2021 Rohlfing ............ A61B 17/8891
11,992,247 B2 * 5/2024 Biedermann ........ A61B 17/708
2005/0015059 A1 1/2005 Sweeney
2006/0075856 A1 4/2006 Tilton
2008/0269768 A1 10/2008 Schwager et al.
2009/0264895 A1 * 10/2009 Gasperut .............. A61B 17/864 606/104
2010/0114174 A1 * 5/2010 Jones ................ A61B 17/7098 606/279
2012/0203287 A1 8/2012 Arambula et al.
2012/0296171 A1 11/2012 Lovell et al.
2015/0257797 A1 9/2015 Biedermann et al.
2019/0298416 A1 * 10/2019 Rezach .............. A61B 17/7007
2020/0022817 A1 1/2020 Crossgrove et al.
2020/0030015 A1 1/2020 Grizzard et al.

FOREIGN PATENT DOCUMENTS

EP 2 269 526 A1 1/2011
JP S62-114884 A 5/1987
JP 2013-509982 A 3/2013
WO WO 2009/015100 A2 1/2009
WO WO 2011/059941 A1 5/2011

OTHER PUBLICATIONS

European Search Report; Application Serial No. 14160107.0; dated Sep. 18, 2014; Completion Date Sep. 9, 2014; 7 Sheets.

* cited by examiner

ADAPTER DEVICE AND SYSTEM INCLUDING AN ADAPTER DEVICE AND A BONE ANCHOR

CROSS-REFERENCE TO RELATED APPLICATION(S)

This application is a continuation of U.S. patent application Ser. No. 17/553,532, filed Dec. 16, 2021, which claims priority to and the benefit of U.S. Provisional Patent Application No. 63/126,758, filed Dec. 17, 2020, the contents of which are hereby incorporated by reference in their entirety, and claims priority from European Patent Application EP 20 215 224.5, filed Dec. 17, 2020, the contents of which are hereby incorporated by reference in their entirety.

BACKGROUND

Field

The application relates to an adapter device for attaching an instrument to a bone anchor, and to a system including such an adapter device and the bone anchor. In particular, the invention relates to an adapter device for use with an instrument, such as a syringe, that is configured to supply bone cement or another fluid or pasty substance to or through the bone anchor.

Description of Related Art

An adapter device of this type and a cannulated bone anchor which is used in connection with the adapter device is known from U.S. Pat. No. 7,717,947. The bone anchor in the form of a bone screw has a screw head and a threaded shank through which an axial bore extends. A plurality of radial bores open into the axial bore. The adapter has an axial bore that is aligned with the axial bore of the threaded shank when the adapter is fitted to an opening in the screw head in a fluid-tight manner. Further, the adapter includes a shoulder along its inner circumference to take up the lower end of the syringe.

U.S. Pat. No. 7,354,442 B2 describes a bone anchor including a bone engaging portion and an elongate guiding portion. The bone engaging portion includes a cannula passage and the elongate guiding portion extends from the bone engaging portion and is configured to guide a device into engagement with the bone engaging portion. Such a device can be, for example, an injector or a delivery mechanism that is configured to deliver a material into the cannula passage of the bone engaging portion.

SUMMARY

It is an object of the invention to provide an improved adapter device, and a system including such an adapter device and a bone anchor, that is robust in use and easy to attach. Moreover the adapter should be particularly useful for supplying bone cement or another fluid or pasty substance to or through the bone anchor.

According to an embodiment, the adapter device for connecting an instrument to a bone anchor is suitable for use with a bone anchor that includes a shank, a head configured to be connected to the adapter device, and a channel extending through the head and at least a portion of the shank. The adapter device includes an elongate adapter main portion defining a longitudinal axis and having a front end configured to be connected to the head of the bone anchor, and a channel extending through the adapter main portion in the longitudinal direction, and a holding member for holding the head of the bone anchor, the holding member configured to at least partially encompass the head and having an inner surface forming a seat for the head. The bone anchor and the adapter device together form a system. Preferably, when the adapter main portion is connected to the head, the channel of the adapter main portion and the channel of the bone anchor are in fluid communication, and more preferably are substantially aligned.

The adapter device and the system may be used, for example, in connection with bone anchors that form the anchoring element of a polyaxial bone anchoring device, such as a polyaxial pedicle screw, for example. A polyaxial bone anchoring device includes a bone anchoring element with a shank and a head, and a receiving part for pivotably receiving the head of the bone anchoring element and for coupling the bone anchoring element to a rod. Some polyaxial bone anchoring devices permit the bone anchoring element to be inserted first into bone, for example, into the pedicle of a vertebra, and to mount the receiving part onto the head of the bone anchoring element thereafter. The adapter device is configured to be directly attached to the head of such a bone anchoring element and to be clamped thereto. After delivery of the bone cement or other fluid or pasty substance, the adapter device can be easily detached and the receiving part can be mounted. Preferably, the head and the seat both have an at least partially spherical shape.

The adapter device is shaped such that, due to increased clamping and tightening surfaces of a portion of the adapter device with respect to the bone anchor, leakage of bone cement or another fluid or pasty substance into the head of the bone anchor may be largely reduced or even prevented.

The adapter device and the bone anchor may be particularly applicable in minimally invasive surgery (MIS). The shape of the adapter device is suitable for implementing the adapter device even when only small incisions of the skin have been made. Moreover, in MIS, the placement of the receiving part onto the head of the bone anchor after the bone anchor has already been provided with bone cement or another fluid or pasty substance can more easily be facilitated.

BRIEF DESCRIPTION OF THE DRAWINGS

Further features and advantages of the invention will become apparent from the detailed description of embodiments by means of the accompanying drawings. In the drawings.

DETAILED DESCRIPTION

Figure 1:
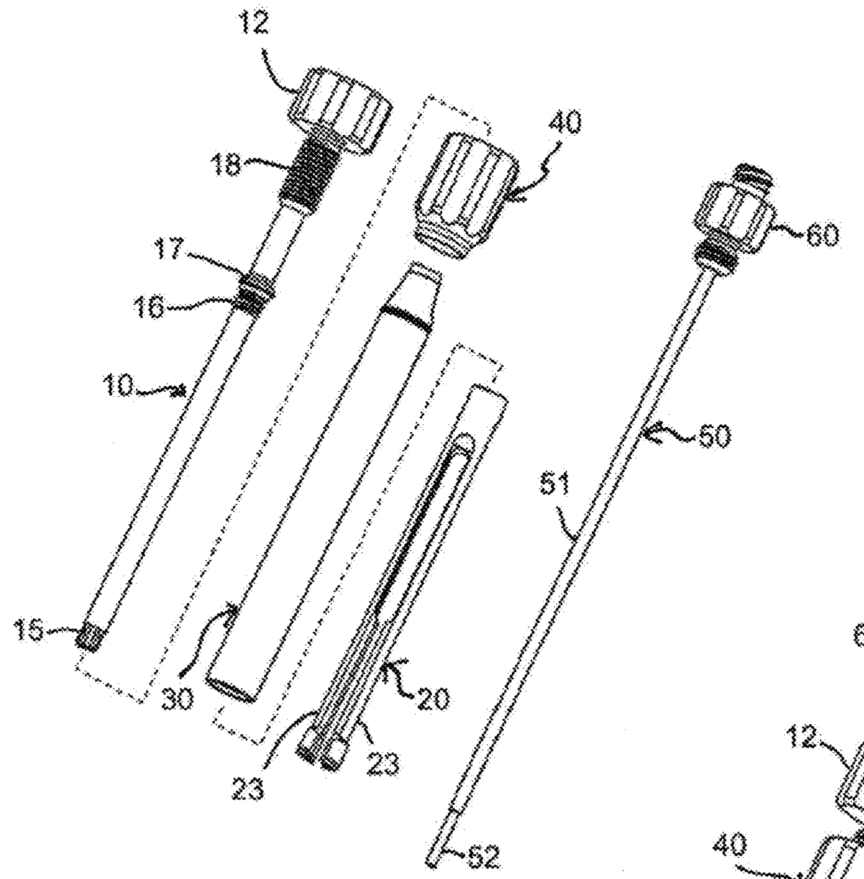
FIG. 1 shows a perspective exploded view of an adapter device according to an embodiment of the invention.
Figure 2:
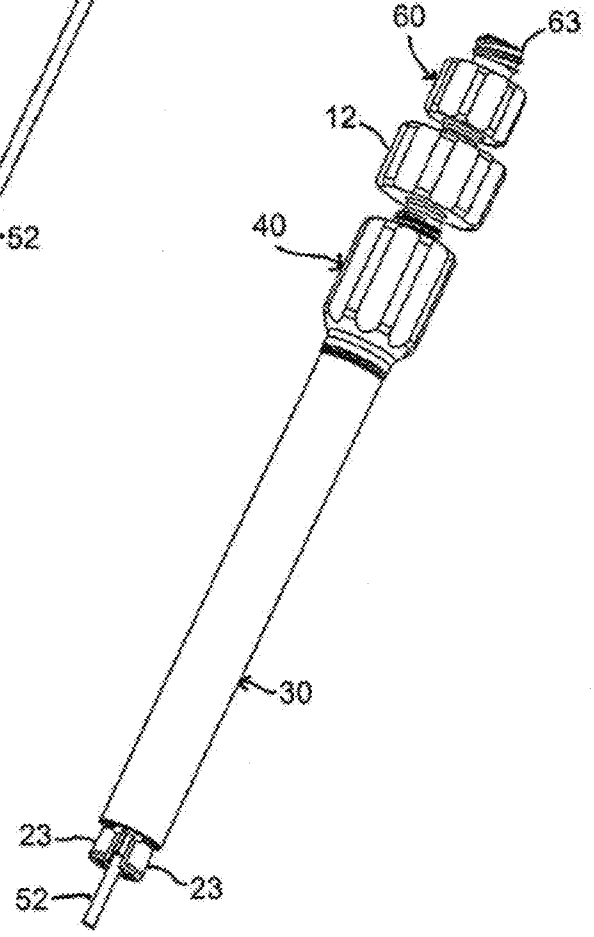
FIG. 2 shows a perspective view of the adapter device of FIG. 1 in an assembled state
Figure 3:
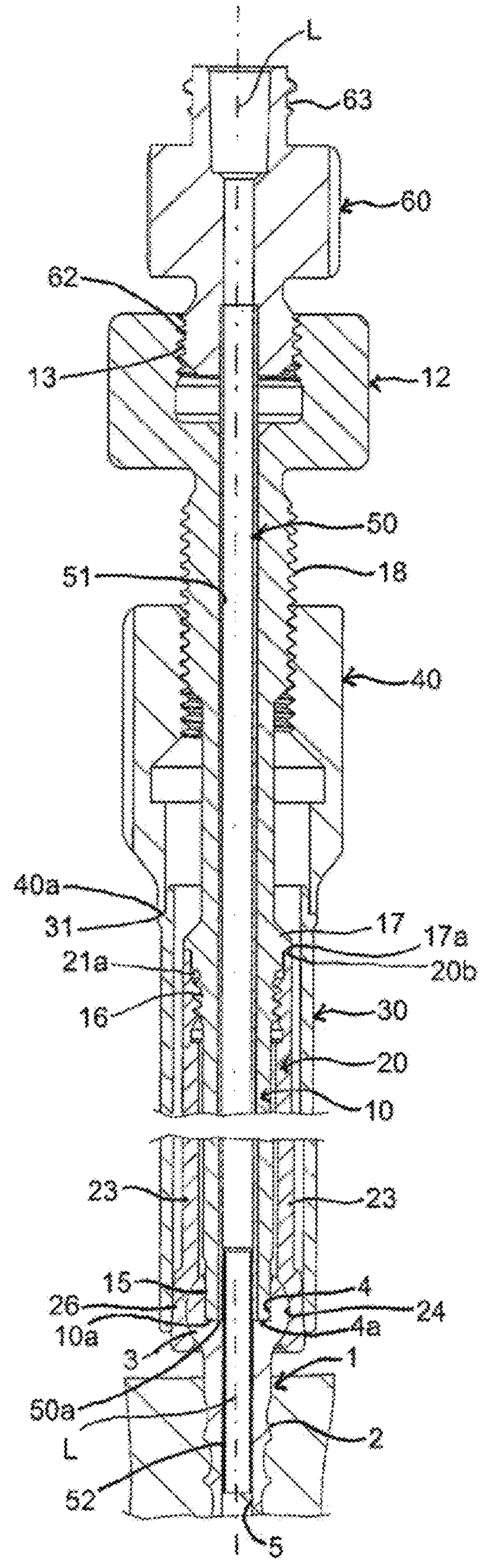
FIG. 3 shows a cross-sectional view of the adapter device together with a bone anchor, the cross-section taken in a plane including a longitudinal axis of the adapter device and extending through a center of arms of a holding portion of the adapter device.

Referring to FIGS. 1 to 3, the adapter device includes an adapter main portion 10 that is configured to be inserted into a head 3 of a bone anchor 1. The adapter main portion 10 is connected to and extends through a holding member 20, which is configured to engage and hold the head 3 of the bone anchor 1. In order to lock the holding member 20 to the head 3, a locking member 30 is provided that extends at least partially around the holding member 20. The locking member 30 is configured to be actuated by an actuating member 40 to assume a first position in which the head 3 is insertable to and removable from the holding member 20, and a second position in which the head 3 is locked in the holding member 20. Furthermore, a supply cannula 50 is configured to extend through the adapter main portion 10 into a shank 2 of the bone anchor 1. The supply cannula 50 is connected to a connection portion 60, to which a device for delivering bone cement or another fluid or pasty substance can be attached.

Referring in greater detail to FIG. 3, a bone anchor 1 which is suitable for use with the adapter device includes a bone engagement structure in at least a portion of the shank 2, such as, for example, a bone thread. The head 3 may have a spherical outer surface portion. This renders the bone anchor suitable for use in a polyaxial bone anchoring device, in which the head is pivotably connected to a receiving part which receives a rod. A recess 4 is formed in a free end surface of the head 3 opposite to a tip (not shown) of the bone anchor 1. The recess 4 may be adapted to be engaged by a tool that is configured to insert the bone anchor 1 into bone. For example, the recess 4 may have a polygonal contour, such as a square or a hexagon, or may have a torx-shape for engagement with a drive tool. The bottom 4*a* of the recess 4 may serve as an abutment for a portion of the adapter main portion 10, and optionally for a portion of the supply cannula 50, as explained below. By the shank 2, a longitudinal axis is defined that may be, for example, a screw axis of the bone anchor. A channel 5 extends fully through the head 3 and at least partially through the shank 2. The channel 5 may be coaxial with the longitudinal axis of the bone anchor. In one example, the channel 5 extends up to the tip (not shown) of the bone anchor, i.e., where the shank 2 is open at the tip. In another example, the channel is closed at the tip or at some distance therefrom. Radial or transverse openings (not shown) may also be provided that extend laterally from the channel 5 to the outside of the shank 2.

Figure 4:
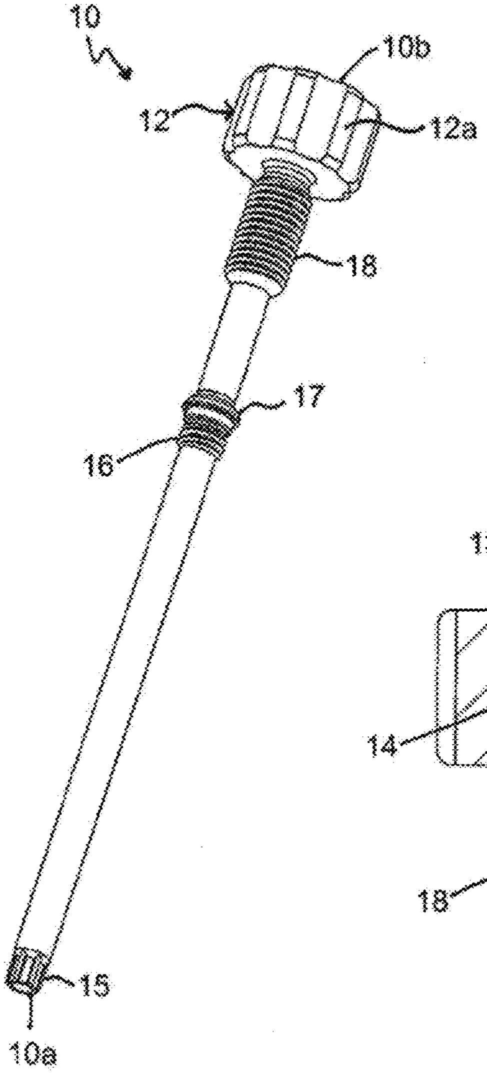
FIG. 4 shows a perspective view of a main portion of the adapter device of FIGS. 1 to 3.
Figure 5:
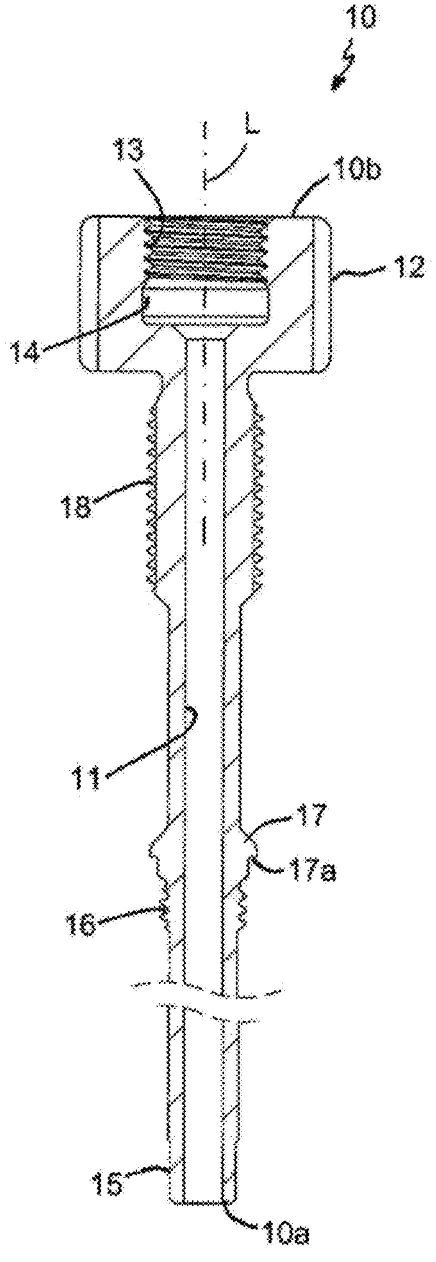
FIG. 5 shows a cross-sectional view of the main portion of FIG. 4, the cross-section taken in a plane including the longitudinal axis of the adapter device.

Referring in greater detail to FIGS. 4 and 5, the adapter main portion 10 is a substantially elongate rod-like member having a front end 10*a* and an opposite rear end 10*b*, and a channel 11 extending fully through the member from the front end 10*a* to the rear end 10*b*. The channel 11 is configured to receive at least a portion of the supply cannula 50 therein. Adjacent to the rear end 10*b*, a gripping portion 12 is formed that may have a greater diameter compared to other sections of the adapter main portion 10. The gripping portion 12 may be provided with a gripping structure 12*a* on its outer surface, such as axially extending grooves. A central longitudinal axis of the channel 11 defines a longitudinal axis L of the whole adapter device. For connecting to the supply cannula 50, or more specifically to the connection portion 60, a threaded bore 13 extends from the rear end 10*b* of the adapter main portion 10 into the gripping portion 12. The threaded bore 13 is configured to be engaged by a portion of the connection portion 60 of the supply cannula 50. Following the threaded bore 13, a coaxial threadless recess 14 with a slightly greater inner diameter than that of the threaded bore 13 may be formed to provide space for adjusting an insertion depth of the supply cannula 50, for example, by screwing the connection portion 60 into the threaded bore 13.

Adjacent to the front end 10*a*, the adapter main portion 10 has a front section 15 that is shaped to fit into the recess 4 of the head of the bone anchor 1. More specifically, an outer contour of the front section 15 may correspond to an inner contour of the recess. For example, as shown in FIG. 4, the outer contour of the front section 15 may be torx-shaped (or hexalobular-shaped) corresponding to a torx-shaped inner contour of the recess. Preferably, the corresponding shapes of the recess and the front section 15 are such that a form-fit connection can be achieved. The axial length of the front section 15 may be at least as long as the axial depth of the recess 4 of the bone anchor. As a result, the adapter main portion 10 may also have the function of a drive tool for inserting the bone anchor 1. Thus, the adapter device may be used for inserting the bone anchor and for subsequent delivery of bone cement or other substance to the bone anchor.

At a distance from the front end 10*a* that corresponds substantially to a location of an end of the holding member

20 when the holding member is attached to the adapter main portion 10 and is around the head 3, a first threaded portion 16 is provided for screwing the holding member 20 onto the adapter main portion 10. Following the first threaded portion 16, an intermediate portion 17 is formed that includes a stop 17*a* which faces the front end 10*a* and against which an end of the holding member 20 abuts when the holding member 20 is correctly mounted onto the adapter main portion 10.

Between the first threaded portion 16 and the gripping portion 12, a second threaded portion 18 is provided on the outer surface of the adapter main portion 10 that serves for cooperation with a corresponding thread of the actuating member 40. The axial length of the second threaded portion 18 is such that the actuating member 40 can be moved along the second threaded portion 18 at least over a length between a first position in which the locking member 30 releases a locking of the head by the holding member 20 and a second position in which the locking member 30 facilitates locking of the head by the holding member 20.

Figure 6:
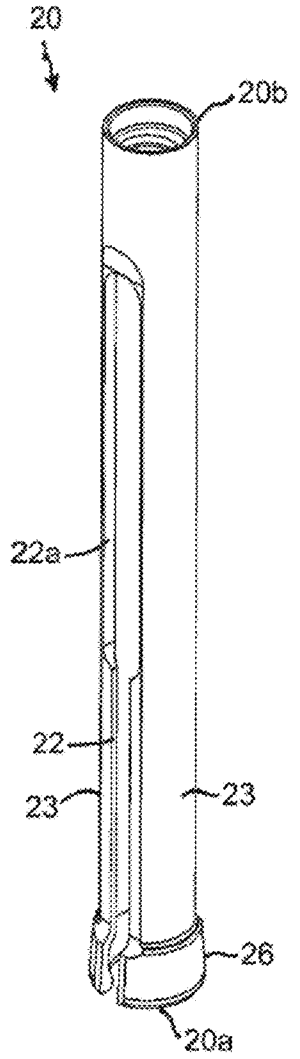
FIG. 6 shows a perspective view from a top of a holding member of the adapter device of FIGS. 1 to 3.
Figure 7:
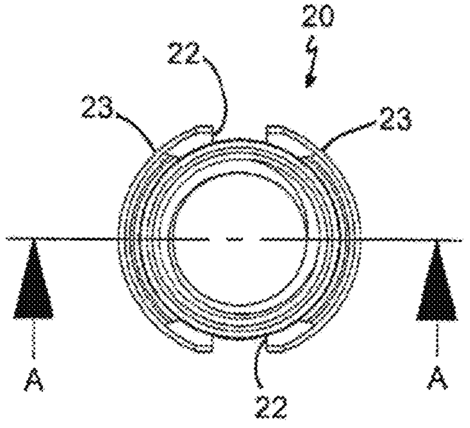
FIG. 7 shows a top view of the holding member of FIG. 6.
Figure 8:
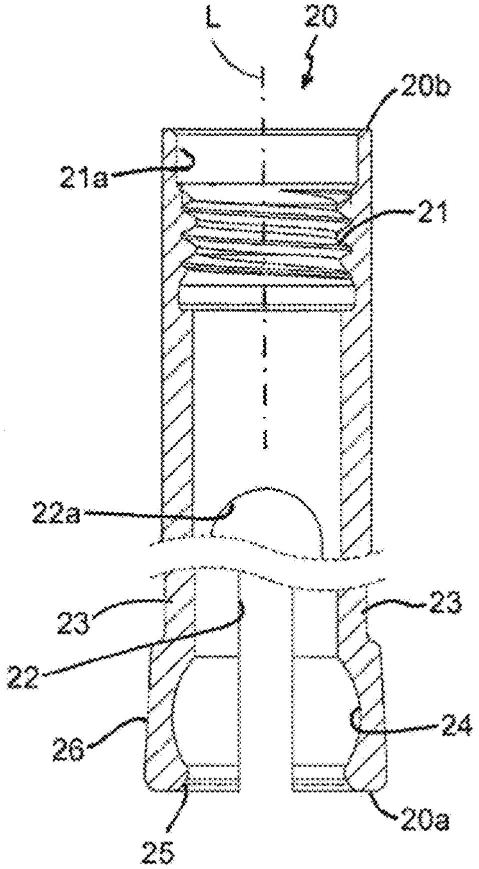
FIG. 8 shows a cross-sectional view of the holding member of FIGS. 6 and 7, the cross-section taken in a plane along line A-A in FIG. 7.

Next, the holding member 20 will be explained, referring additionally to FIGS. 6 to 8. The holding member 20 is substantially sleeve-shaped, and has a front end 20*a* and a rear end 20*b*. A inner diameter of the sleeve is such that a rod-shaped region of the adapter main portion 10 can extend therethrough.

At a distance from the rear end 20*b*, an internally threaded section 21 is provided that is configured to cooperate with the first threaded section 16 of the adapter main portion 10. The internally threaded section 21 has a slightly smaller inner diameter than an inner diameter at the rear end 20*b* of the holding member 20. By the reduction of the inner diameter, an enlarged space 21*a* is formed up to the rear end 20*b* that is configured to receive part of the intermediate portion 17 of the adapter main portion 10, as shown in FIG. 3. Moreover, the holding member 20 includes a slot 22 that is open to the front end 20*a* and that extends transversely through the holding member 20 along a plane including the longitudinal axis L, such that two arms 23 are formed by the slot 22. The slot may widen into a substantially elongate opening 22*a* that is closed towards the rear end 20*b*. The opening 22*a* may provide for greater flexibility of the arms 23. The slot 22 renders the arms 23 resilient, i.e., compressible toward each other and spreadable apart from each other. The width of the slot 22 may be such that, when the head 3 is introduced into and held in a seat 24, the head 3 may be preliminarily held by friction even without a force imparted from the locking member 30.

At a distance from the front end 20*a*, there is an inner spherically segment-shaped section which forms the seat 24 for the head 3 of the bone anchor 1. A radius of the inner spherical segment-shaped section 24 substantially matches the shape of an outer surface portion of the head 3. As can be seen in detail in FIG. 8, a region with a largest diameter of the sphere defined by the spherical segment-shaped section 24 is between an upper edge and a lower edge of the seat 24. Hence, when the head 3 is received in the seat 24 and the arms 23 are pressed together, the head 3 is also held in a form-fit manner in the seat 24. Between the seat 24 and the front end 20*a*, an outwardly tapering section 25 may be formed that may facilitate the insertion of the head 3 into the seat 24.

An outer surface portion 26 extending from the front end 20*a* over an axial length or height that is greater than the axial extension or height of the seat 24, increases in a manner such that the outer diameter of the outer surface portion increases towards the front end 20*a*. By means of this, when the locking member 30 is moved towards the front end 20*a* of the holding member 20, an increasing pressure can be generated that acts onto the head 3 of the bone anchor 1 when the head is held in the seat 24. In addition, the outer surface portion 26 may have a greater outer diameter than other portions of the holding member 20.

The length of the holding member 20 is such that, when the holding member 20 is screwed onto the first threaded portion 16 of the adapter main portion 10 until the rear end 20*b* abuts against the stop 17*a*, the front end 10*a* of the adapter main portion 10 abuts against the bottom 4*a* of the recess 4 of the head 3 of the bone anchor 1, and the head 3 is fully received in the seat 24.

Figure 9:
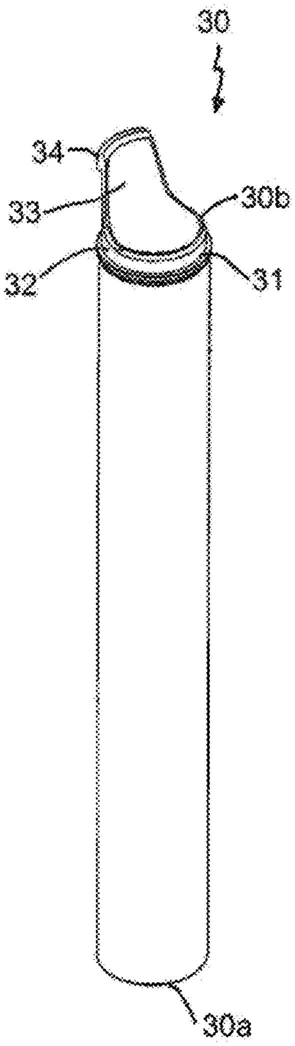
FIG. 9 shows a perspective view from a top of a locking member of the adapter device of FIGS. 1 to 3 that facilitates locking of the holding member.
Figure 10:
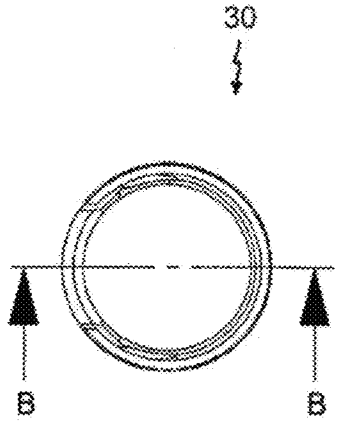
FIG. 10 shows a top view of the locking member of FIG. 9.
Figure 11:
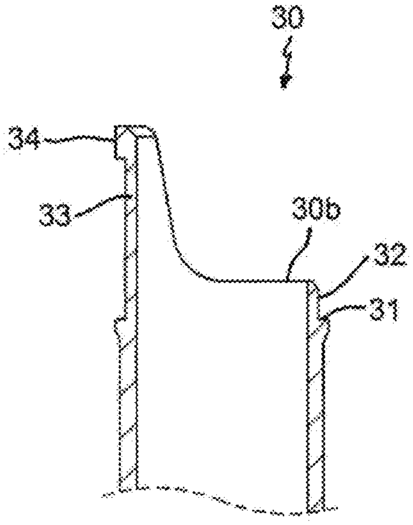
FIG. 11 shows a cross-sectional view of an upper portion of the locking member of FIGS. 9 and 10, the cross-section taken in a plane along line B-B in FIG. 10.

Referring now additionally to FIGS. 9 to 11, the locking member will be described. The locking member 30 is formed as a substantially cylindrical sleeve with a front end 30*a* and an opposite rear end 30*b*. An inner diameter of the locking member 30 is such that, as can be seen in FIG. 3, the holding member 20 can extend through the locking member 30. Adjacent to the front end 30*a*, an inner surface portion of the locking member may taper slightly outwardly, such that the locking member 30 can smoothly slide on the outer surface 26 of the holding member 20. The remaining portions of the locking member 30 may have a cylindrical inner surface.

Close to the rear end 30*b* of the locking member 30, a circumferentially protruding and upwardly facing annular surface 31 is formed that acts as an abutment for the actuating member 40 as described below. Between the annular surface 31 and the rear end 30*b*, the sleeve forming the locking member 30 includes a circular rim 32 with a smaller outer diameter than the annular surface 31. Moreover, a flap-like extension or a flap 33 projects above the rim 32. The flap 33 has a substantially cylindrical inner surface and a substantially cylindrical outer surface. A width of the flap 33 adjacent to the rim 32 may be larger than a width of a free end of the flap 33. Furthermore, at the free end, the flap 33 includes an outwardly extending circumferential projection 34 that is configured to cooperate with a portion of the actuating member 40 as described below. The height of the flap 33 between the annular surface 31 and the outward projection 34 corresponds substantially to the height of a corresponding inner portion of the actuating member 40 in an axial direction.

An axial length of the locking member 30 is such that, in a first position of the actuating member 40 that corresponds to a first configuration of the locking member relative to the holding member, the front end 30*a* of the locking member 30 is positioned at a distance from the front end 20*a* of the holding member 20. In the first configuration, the arms 23 of the holding member are permitted to spread to allow insertion of the head 3 of the bone anchor 1. Furthermore, the axial length of the locking member 30 is such that in a second position of the actuating member 40 that corresponds to a second configuration, the front end 30*a* of the locking member 30 is closer to the front end 20*a* of the holding member 20, so that the locking member 30 compresses the arms 23 of the holding member 20 to clamp an inserted head 3 in the holding member 20.

Figure 12:
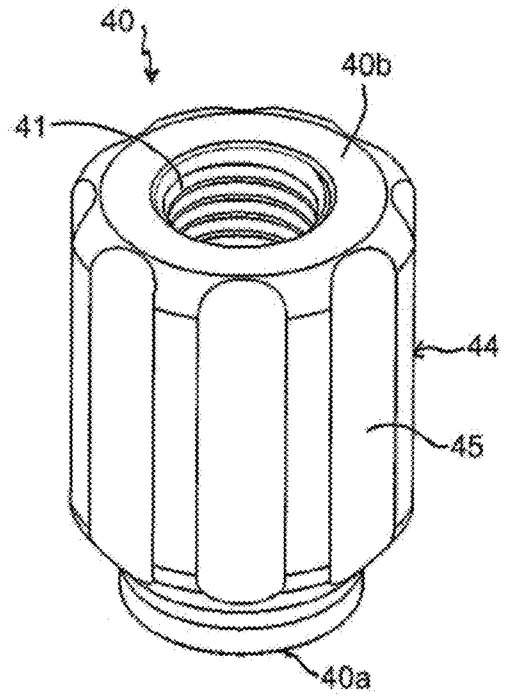
FIG. 12 shows a perspective view from a top of an actuating member of the adapter device of FIGS. 1 to 3 that is configured to actuate the locking member.
Figure 13:
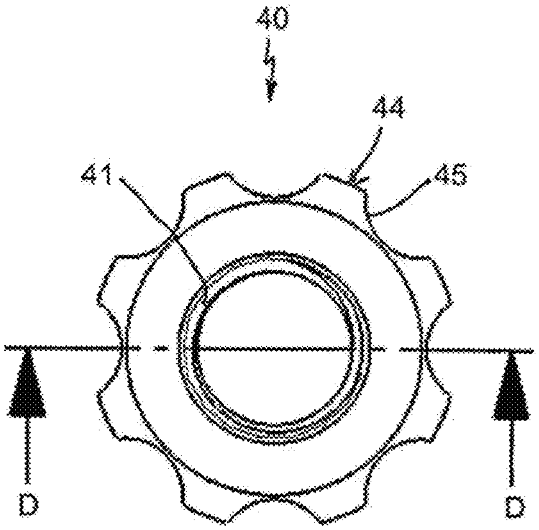
FIG. 13 shows a top view of the actuating member of FIG. 12.
Figure 14:
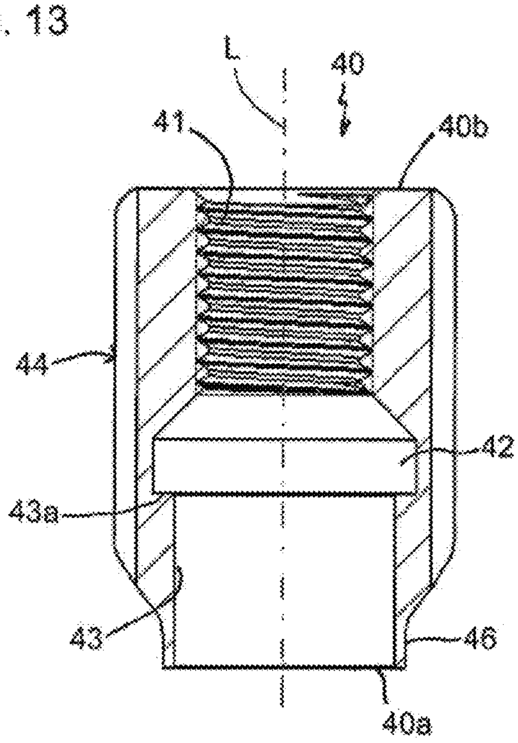
FIG. 14 shows a cross-sectional view of the actuating member of FIGS. 12 and 13, the cross-section taken in a plane along line D-D in FIG. 13.
Figure 15:
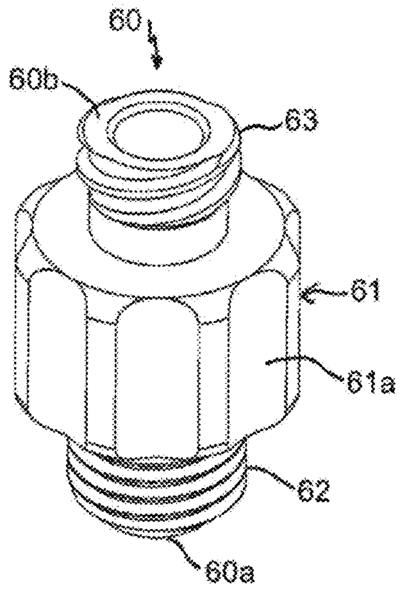
FIG. 15 shows a perspective view from a top of a connection portion of a supply cannula of the adapter device of FIGS. 1 to 3.
Figure 16:
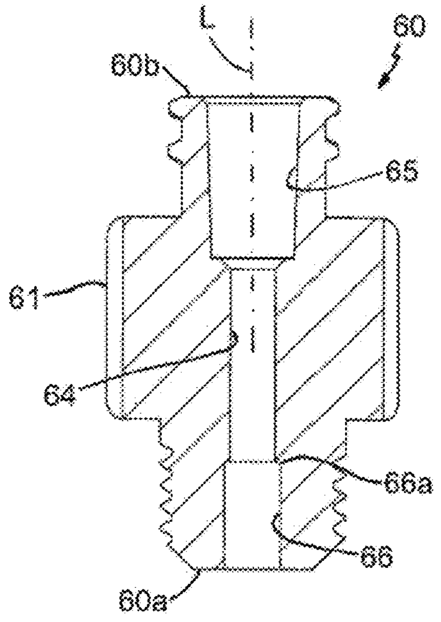
FIG. 16 shows a cross-sectional view of the connection portion of FIG. 15, the cross-section taken in a plane including the longitudinal axis of the adapter device.
Figure 17:
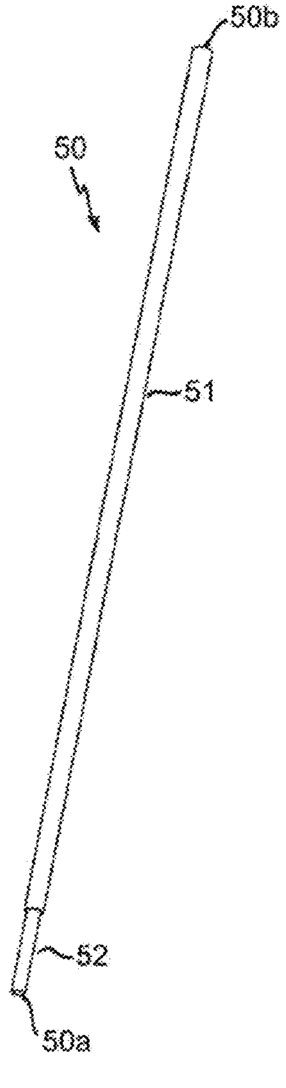
FIG. 17 shows a perspective view of the supply cannula of the adapter device of FIGS. 1 to 3.
Figure 18:
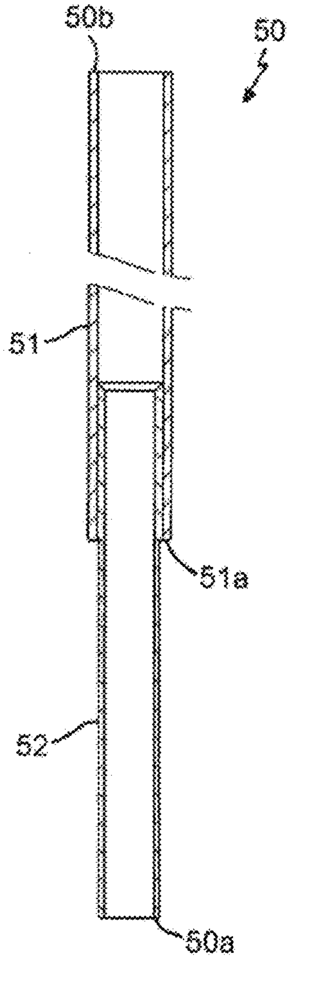
FIG. 18 shows a cross-sectional view of the supply cannula of FIG. 17, the cross-section taken in a plane including the longitudinal axis of the adapter device.

Referring to FIGS. 12 to 14, the actuating member 40 includes a front end 40*a* and an opposite rear end 40*b*. At the rear end, a coaxial threaded bore 41 is formed that cooperates with the external second threaded portion 18 of the adapter main portion 10. Hence, the threaded bore 41 permits the actuating member 40 to be screwed along the second threaded portion 18 of the adapter main portion 10. Adjacent to the threaded bore 41, there is an inner substantially cylindrical section 42 with a diameter that may be greater than an outer diameter of the threaded portion 41, such that an outer diameter of the second threaded section 18 of the adapter main portion 10 can extend therethrough.

Between the cylindrical section 42 and the front end 40*a*, a second cylindrical section 43 is provided with a smaller diameter than the cylindrical section 42, such that an annular shoulder 43*a* is provided within the actuating member 40. An inner diameter of the cylindrical section 43 is such that the adapter main portion 10 can extend therethrough with its rod-shaped part. In addition, the flap 33 of the locking member 30 can also extend through the second cylindrical section 43 (not shown). When the locking member 30 is inserted into the actuating member 40, the flap 33 hangs on the shoulder 43*a* with a lower side of the circumferential outward projection 34, while the front end 40*a* of the actuating member 40 abuts against the annular surface 31 of the locking member 30. By means of this, the locking member 30 is configured to be connected to the actuating member 40 via the flap 33, such that the actuating member 40 can rotate with respect to the locking member 30, but the locking member 30 is fixed against displacement in an axial direction relative to the actuating member 40. Thus, the flap 33 functions as a follower. As a result, an axial advancement of the actuating member 40 results in a corresponding axial advancement of the locking member 30.

The actuating member 40 further includes an upper substantially cylindrical outer section 44 adjacent to the rear end 40*b* with a plurality of axial grooves 45 that facilitate gripping. Further, the actuating member 40 includes a second outer cylindrical section 46, with an outer diameter such that the outer surface of the second portion may be substantially flush with the annular surface 31 of the locking member 30.

Referring further to FIGS. 15 to 18, the supply cannula 50 and the connection portion 60 will be explained. The connection portion 60 has a front end 60*a* and an opposite rear end 60*b*. Between the front end 60*a* and the rear end 60*b*, a gripping section 61 is provided that is substantially cylindrical with a gripping structure, such as axially extending grooves 61*a*. Adjacent to the front end 60*a*, a cylindrical section 62 with an external thread is provided that may have a reduced outer diameter compared to the gripping portion 61 and that is configured to be screwed into the threaded bore 13 in the gripping portion 12 of the adapter main portion 10. Opposite to the threaded portion 62 adjacent to the rear end 60*b*, a connecting portion 63 is formed that is configured to connect to a corresponding connecting portion (not shown) of a syringe or a cartridge or other fluid delivering device. The connecting portion 63 may be, for example, a connecting portion with a standardized connection structure, for example a Luer lock connection structure.

A longitudinal channel 64 extends from the rear end 60*b* to the front end 60*a*. Adjacent to the rear end 60*b*, there is a widened passage 65 that is wider at the rear end 60*b* than at the transition to the intermediate portion of the channel 64. The widened portion 65 may be, for example, conically widening towards the rear end 60*b*. By means of this, the widened section 65 can be engaged by a corresponding conical tip of a fluid delivering device, such as a syringe. Adjacent to the front end 60*a*, a cylindrical section 66 that has a slightly greater inner diameter than the intermediate section of the channel 64 is provided, such that a step or shoulder 66*a* is formed at the transition between the section 66 and the intermediate section of the channel 64. The shoulder 66*a* forms an abutment for the rear end of the supply cannula 50.

The supply cannula 50 is formed as an elongate tube with a front end 50*a* and an opposite rear end 50*b*. Preferably, the supply cannula is a rigid cylindrical tube. As can be seen in particular in FIG. 18, the supply cannula 50 is made of a first tube 51 with a larger inner and outer diameter, and a second smaller tube 52 that is inserted at one end into the first tube 51 and firmly held therein, for example, by a press-fit connection. Hence, the rear end 50*b* of the supply cannula is at the first tube 51, and the front end 50*a* is at the second tube 52. A front end 51*a* of the first tube forms a step in the outer surface of the supply cannula 50 that is configured to abut against the bottom 4*a* of the recess 4 in the head 3 of the bone anchor 1. The supply cannula 50 may be fixedly connected to the connection portion 60. This is achieved by inserting the supply cannula 50 into the channel section 66 of the connection portion 60 until the rear end 50*b* of the supply cannula abuts against the shoulder 66*a*, as shown in FIG. 3. For example, the supply cannula 50 can be connected in a press-fit manner to the connection portion 60.

An outer diameter of the first tube 51 corresponds substantially to an inner diameter of the channel 11 of the adapter main portion 10. An outer diameter of the second tube 52 is such that the second tube 52 can be inserted into the channel 5 of the bone anchor 1. The two-tube assembly of the supply cannula 50 may allow exchanging of the second tube 52 with another second tube having, for example, another diameter. Hence, several second tubes 52 can be provided with differing outer diameters corresponding to differing channel widths 5 of various bone anchors. It shall be noted that, while the supply cannula 50 in the embodiment has two tubes, the supply cannula can also be made of one single tube, for example, with a reduced diameter at the front portion.

As shown in FIG. 3, a total length of the supply cannula is such that the second tube 52 can be inserted to some extent into the channel 5 of the bone anchor when the adapter device is fully assembled and attached to the bone anchor. The position of the step 51*a* is adjustable by screwing the gripping portion 60 forward or backward in the threaded hole 13. By means of this, it can be ensured that the step 51*a* on the supply cannula 50 abuts against the bottom 4*a* of the recess 4 of the head 3.

The parts and portions of the bone anchor and of the adapter device may be made of any material that is biocompatible. Preferred materials are titanium or stainless steel, or any biocompatible metal or metal alloy or plastic material. For a biocompatible alloy, a NiTi alloy, for example Nitinol, may be used. Other materials that can also be used are magnesium or magnesium alloys. Biocompatible plastic materials that can be used may be, for example, polyether ether ketone (PEEK) or poly-L-lactide acid (PLLA). The parts can be made of the same or of different materials from one another.

The adapter main portion 10, the holding member 20, and the locking member 30 with actuating member 40 may be preassembled, before inserting the supply cannula 50 mounted to the connection portion 60. For assembling, the holding member 20 is screwed onto the first threaded section 16 of the adapter main portion 10. Then, the locking member 30, that has been snapped with the flap 33 into the actuating member 40, is mounted from the front end 20*a* of the holding member onto the adapter main portion 10, until the threads of the threaded bore 41 of the actuating member 40 and the second threaded section 18 of the adapter main portion 10 are engaged. It shall be noted that, for mounting the locking member 30, the arms 23 of the holding member 20 may be slightly compressed.

In clinical use, first, the bone anchor 1 is inserted into bone or into a vertebra. For example the bone anchor 1 can be the anchoring element of a polyaxial pedicle screw which is inserted into a pedicle of a vertebra. In particular, in the case of a weak bone structure for example due to osteoporosis, it may be advantageous or even required to stabilize the bone anchor in the bone or the vertebra using bone cement. The bone cement or any other fluid or pasty substance can therefore be applied to the bone anchor via the adapter device.

Figure 19A:
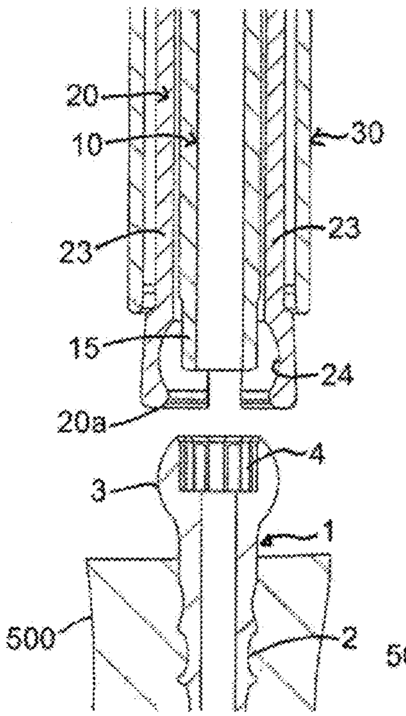
FIGS. 19*a* to 19*e* show steps of mounting the adapter device of FIGS. 1 to 3 to a head of a bone anchor and inserting the supply cannula into the head.

Referring to FIGS. 19*a* to 19*e*, the mounting of the adapter device to a bone anchor 1 that has been inserted into bone or a vertebra 500 is shown. First, as depicted in FIG. 19*a*, the adapter device is in the first configuration in which the arms 23 of the holding member 20 are or can be spread apart to allow the head 3 to enter between them. The front section 15 of the adapter main portion protrudes into the space between the arms that include the seat 24. The locking member 30 is in the first position, which is a retracted position, such that the arms are not compressed.

Figure 19B:
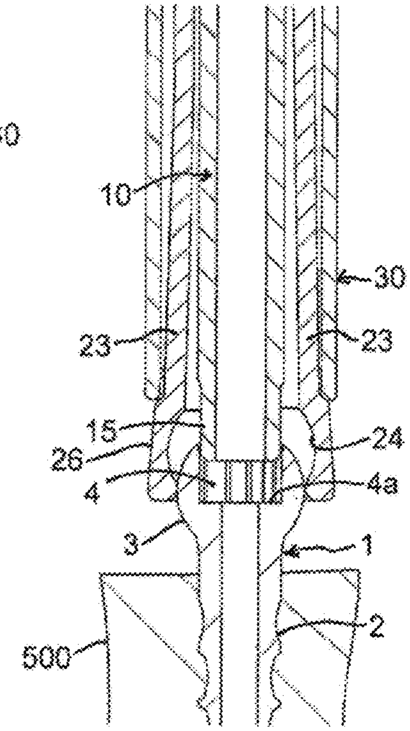
Figure 19C:
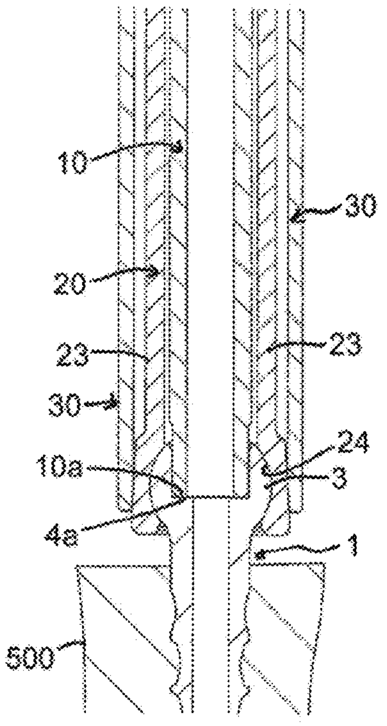

Next, as shown in FIG. 19*b*, the arms 23 of the holding member are placed over the head 3 of the bone anchor, such that the head 3 can enter between them in the region of the seat 24. Simultaneously, the end portion 15 of the adapter main portion 10 enters into the recess 4 of the head 3 of the bone anchor 1. Then, as shown in FIG. 19*c*, when the head 3 has fully entered the seat 24 and simultaneously the front end 10*a* of the adapter main portion abuts against the bottom 4*a* of the recess 4 of the head 3, the head 3 is clamped between the arms 23. Depending on their relative sizes, the friction between the head 3 and the seat 24 may be enough to prevent falling off of the adapter device from the bone anchor. To lock the head 3 in the holding member, the locking member 30 is advanced towards the front end 20*a* of the holding member 20 to a second axial position in which the head 3 is locked. As the lower part of the locking member slides along the tapered outer surface 26 of the arms 23, the arms are pressed together to lock the head in the seat 24. Hence, the second configuration of the locking member relative to the holding member is a locked configuration.

Figure 19D:
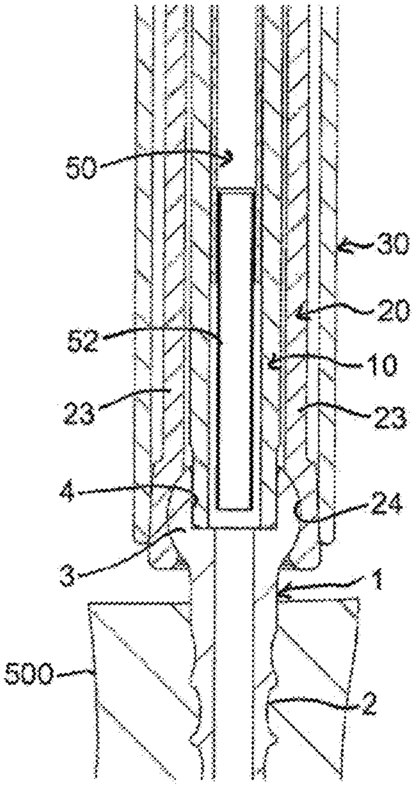
Figure 19E:
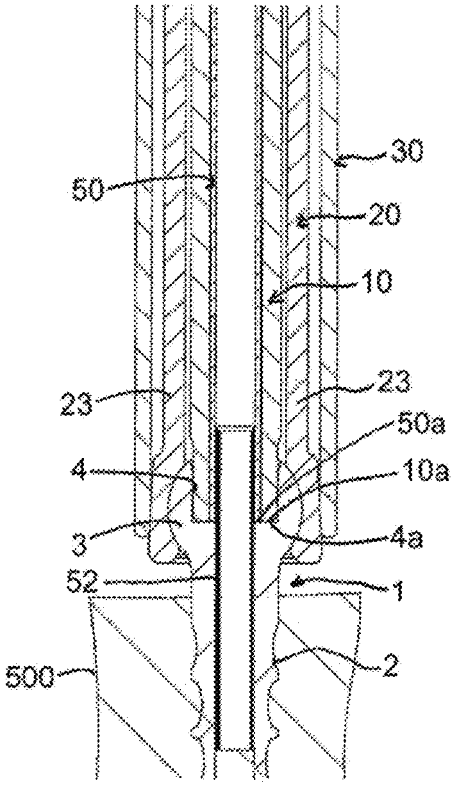

Thereafter, the supply cannula 50 is inserted through the adapter main portion 10 from the rear end 10*b* of the adapter main portion using the connection portion 60 (see, e.g., FIG. 19*d*). The supply cannula 50 is advanced until the step 51*a* on its outer surface abuts against the bottom 4*a* of the recess 4 in the head 3, as shown in FIG. 19*e*. In the mounted state, the front portion 10*a* of the adapter main portion 10 and the step 51*a* of the supply cannula firmly press onto the bottom 4*a* of the recess 4. Thereby a fluid-tight sealing of the head 3 with respect to the channel 5 in the shank 2 is achieved. Since the two portions abut against the bottom 4*a* of the recess 4, a sealing efficiency is increased.

Figure 20:
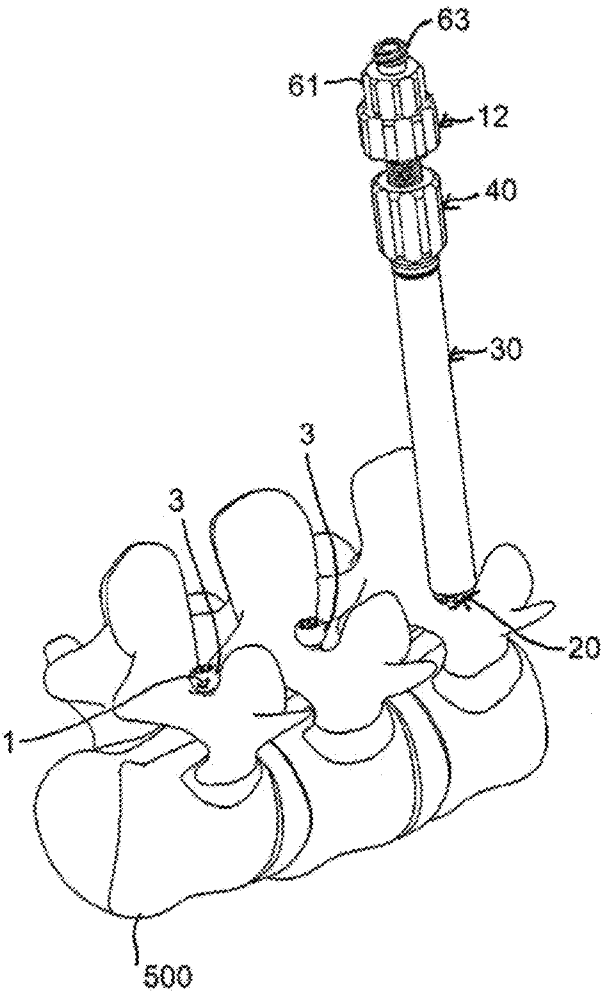
FIG. 20 shows a perspective view of the adapter device of FIGS. 1 to 3 attached to a bone anchor inserted into a pedicle of a vertebra.
Figure 21:
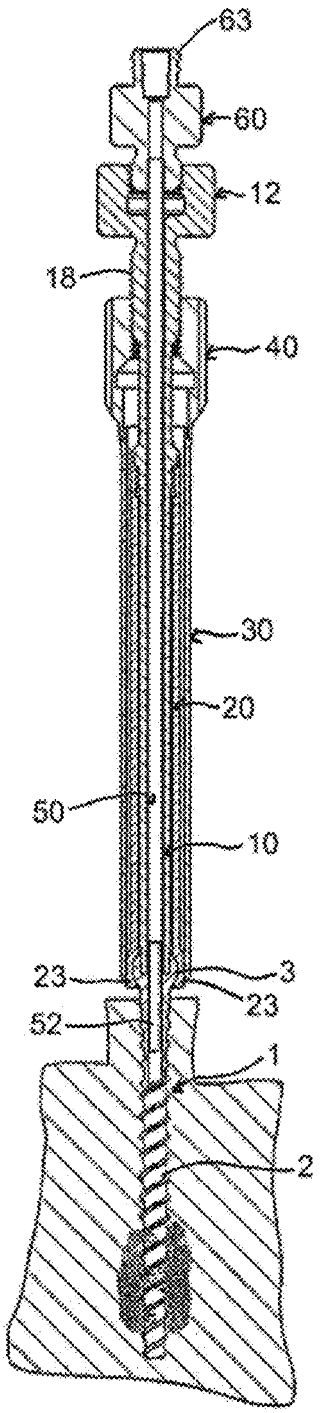
FIG. 21 shows a cross-sectional view of the adapter device attached to a head of a bone anchor that has been inserted into the pedicle of a vertebra, for example, as shown in FIG. 20, wherein the cross-section is taken in a plane including the longitudinal axis of the adapter device, and wherein bone cement or another fluid or pasty substance has been supplied to the bone anchor.

FIG. 20 shows the adapter device attached to one of a plurality of bone anchors 1 each inserted into a pedicle of a respective vertebra. A syringe or a cartridge with bone cement or another fluid or pasty substance may then be attached to the portion 63 of the connection portion 60 of the supply cannula 50 (not shown). Then, the bone cement or the other substance can be injected through the supply cannula 50 into the channel 5 of the bone anchor. FIG. 21 shows bone cement or other substance exiting through radial openings from the channel 5 of the bone anchor 1 into the surrounding bone material.

Thereafter, the supply cannula 50 is removed and the locking member 30 can be retracted again to its first position where the arms are not compressed. Finally, the adapter device can be removed.

The plurality of bone anchors can be provided with bone cement one after another. Then, the receiving parts of the polyaxial bone anchoring devices can be attached to the bone anchors, respectively, and a stabilizing rod can be inserted and fixed.

Various further modifications that can be made include, for example, fixation and/or advancement structures other than threads for mounting the holding member to the adapter main portion, or for mounting and permitting axial advancement of the actuating member relative to the adapter main portion, or between the connection portion of the supply cannula and the adapter main portion. The supply cannula may have a constant diameter over its whole length and can be sized, for example, for insertion into the channel of the bone anchor. In this case, an abutment of a portion of the supply cannula against the head of the bone anchor may not take place. The head and the seat may have a shape other than a fully or partially spherical shape.

The front section of the adapter main portion does not have to have a shape corresponding to the recess in the head, it may be sufficient for the front portion to just fit into the recess. A form fit connection is not necessary.

The parts are also not limited to their detailed shapes as depicted in the embodiments. For the anchoring element, all kinds of bone anchors, such as screws, nails, and hooks, that are somehow cannulated, may also be used.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An adapter device for connecting an instrument to a bone anchor that comprises a shank and a head and that defines a channel that extends through the head and at least a portion of the shank, the adapter device comprising:

an elongate main portion having a longitudinal axis, a first end with a surface that is directly engageable with the head, an opposite second end, and a channel that extends longitudinally through the main portion;

a holding member comprising an inner surface forming a seat for the head; and a supply cannula configured to move axially through the entire channel of the main portion and to be held at a plurality of axial positions relative to the main portion.

2. The adapter device of claim 1, further comprising a locking member configured to act on the holding member to adjust the holding member from a first configuration, where the seat is expandable for inserting the head, to a second configuration where expansion of the seat is restricted to hold the head in the seat.

3. A system comprising the adapter device of claim 1 and the bone anchor that comprises the shank, the head, and the channel that extends through the head and at least a portion of the shank.

4. The adapter device of claim 1, wherein the supply cannula comprises a first threaded portion configured to adjustably engage with a second threaded portion on another portion of the adapter device such that the supply cannula is movable between the plurality of axial positions via the first threaded portion.

5. The adapter device of claim 1, wherein the supply cannula is configured to adjustably engage the main portion to selectively move between the plurality of axial positions.

6. The adapter device of claim 1, wherein the supply cannula comprises a connecting portion configured to detachably and fluidically connect to a fluid delivering device.

7. The adapter device of claim 1, wherein the supply cannula comprises a first portion having a first outer width and a second portion having a second outer width smaller than the first outer width, and protruding from the first portion, and wherein the second portion defines an end of the supply cannula.

8. The adapter device of claim 1, wherein the holding member is shaped and sized to extend over a majority of a longitudinal length of the main portion.

9. The adapter device of claim 1, wherein the holding member is configured to hold the head in the seat against the first end of the main portion while a first portion of the seat is axially spaced apart from the first end of the main portion.

10. An adapter device for connecting an instrument to a bone anchor that comprises a shank and a head and that defines a channel that extends through the head and at least a portion of the shank, the adapter device comprising:

an elongate main portion having a longitudinal axis, a first end with a surface that is directly engageable with the head, an opposite second end, and a channel that extends longitudinally through the main portion;

a holding member comprising an inner surface forming a seat for the head; and a supply cannula configured to move through the entire channel of the main portion, the supply cannula comprising a first portion and a second portion extending from a first end of the first portion in a direction away from the first portion, wherein the first end of the first portion is positionable at a same axial height as the first end of the main portion, and wherein an outer width of the second portion is smaller than an outer width of the first portion.

11. The adapter device of claim 10, wherein a first outer width of the first portion is greater than a second outer width of the second portion such that a step is defined between the first portion and the second portion.

12. The adapter device of claim 10, wherein the first portion comprises a first tube defining the first end, and wherein the second portion comprises a second tube that is inserted into the first tube at the first end.

13. The adapter device of claim 10, wherein the supply cannula comprises a connection portion having a first end and a second end, wherein a second end of the first portion, opposite to the first end of the first portion, is inserted into the first end of the connection portion, and wherein the connection portion is configured to engage with another portion of the adapter device, and to fluidically connect to a fluid delivering device.

14. The adapter device of claim 10, wherein the adapter device is adjustable from a first configuration, whereby the seat of the holding member is expandable for inserting the head, to a second configuration, whereby expansion of the seat is restricted to hold the head in the seat, while an axial position of the holding member relative to the main portion remains constant.

15. The adapter device of claim 14, wherein the adapter device further comprises a locking member configured to act on the holding member to adjust the holding member from the first configuration to the second configuration.

16. A kit, comprising:

a bone anchor comprising a shank and a head, wherein the bone anchor defines a channel extending through the head and at least a portion of the shank; and an adapter device, comprising:

an elongate main portion having a longitudinal axis, a first end with a surface that is directly engageable with the head, an opposite second end, and a channel that extends longitudinally through the main portion, a holding member having an inner surface forming a seat for the head, and a supply cannula insertable into the channel of the main portion, wherein, when the head is in the seat, the supply cannula is configured to move through the first end of the main portion to the head, and to directly engage with an abutment of the head such that axial movement of the supply cannula relative to the bone anchor is limited by the abutment.

17. The kit of claim 16, wherein the abutment of the head is defined by a recess in the head that has a first width that is greater than a second width of a portion of the channel that extends from the recess.

18. The kit of claim 16, wherein the first end of the main portion and the supply cannula are configured to contact the abutment of the head to create a fluid-tight seal between a channel of the supply cannula and the channel of the bone anchor.

19. The kit of claim 16, wherein the supply cannula comprises:

a first portion having a first end configured to directly engage with the abutment of the head; and a second portion that extends from the first end of the first portion and is shaped and sized to extend through a portion of the channel extending through a portion of the shank.

20. The kit of claim 16, wherein an end portion of the holding member defines an opening that is configured to expand to receive the head of the bone anchor into the seat, and wherein the adapter device comprises a locking member that is selectively movable relative to the holding member between a first position, whereby the locking member restricts the opening of the end portion from expanding, and a second position whereby the opening of the end portion is expandable.

* * * * *